(12) United States Patent
Bharmi et al.

(10) Patent No.: US 9,433,793 B2
(45) Date of Patent: Sep. 6, 2016

(54) SYSTEM AND METHOD FOR ACCURATELY DETECTING CARDIAC EVENTS USING MULTI-THRESHOLD PROCESSING

(75) Inventors: Rupinder Bharmi, Canyon Country, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 2347 days.

(21) Appl. No.: 12/264,131

(22) Filed: Nov. 3, 2008

(65) Prior Publication Data

US 2010/0114194 A1    May 6, 2010

(51) Int. Cl.
- *A61B 5/04* (2006.01)
- *A61N 1/37* (2006.01)
- *A61B 5/0452* (2006.01)
- *A61B 5/0456* (2006.01)

(52) U.S. Cl.
CPC ......... *A61N 1/3704* (2013.01); *A61B 5/04012* (2013.01); *A61B 5/0456* (2013.01); *A61B 5/04525* (2013.01)

(58) Field of Classification Search
CPC .. A61B 5/0452; A61B 5/046; A61B 5/0464; A61B 5/04012; A61B 5/0456; A61B 5/0472; A61B 5/0468; A61B 5/02405; A61B 5/0402; A61N 1/3702; A61N 1/3621; A61N 1/3704; A61N 1/37; A61N 1/3706

USPC .............................. 600/515, 509, 521; 607/9
See application file for complete search history.

(56) References Cited

U.S. PATENT DOCUMENTS

| | | | | |
|---|---|---|---|---|
| 2001/0031994 A1* | 10/2001 | Mika | .................... | A61N 1/3962 607/9 |
| 2005/0113705 A1* | 5/2005 | Fischell | ............... | A61B 5/0031 600/515 |
| 2005/0131470 A1* | 6/2005 | Vitali | ................. | A61N 1/36542 607/9 |
| 2007/0293778 A1* | 12/2007 | Fischell | ............... | A61B 5/0031 600/515 |
| 2009/0099468 A1* | 4/2009 | Thiagalingam | ...... | A61B 5/0452 600/515 |

\* cited by examiner

*Primary Examiner* — Michael Kahelin
*Assistant Examiner* — Minh Duc Pham

(57) ABSTRACT

A system and method provide precise detection of the time of occurrence of a cardiac event of a heart. The method comprises the steps of sensing electrical activity of the heart to generate an electrogram of the heart and applying the electrogram to an event detector having a plurality of spaced apart thresholds. The thresholds are selected such that the electrogram has an amplitude for crossing at least one of the thresholds. The method further comprises determining a characteristic identifying feature of the electrogram at each threshold crossing of the electrogram, comparing the determined characteristic identifying features to an electrogram template, and identifying the time of occurrence of the cardiac event based upon the comparison.

20 Claims, 3 Drawing Sheets

SYSTEM AND METHOD FOR ACCURATELY DETECTING CARDIAC EVENTS USING MULTI-THRESHOLD PROCESSING

FIELD OF THE INVENTION

The present invention generally relates to systems and methods for accurately detecting cardiac events and implantable cardiac stimulation devices utilizing such systems and methods. The present invention more particularly relates to such methods, systems, and devices for accurately detecting the beginning of cardiac events by multithreshold retrospective analysis of stored electrograms.

BACKGROUND

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or evoked responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or evoked responses are sensed between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardiac defibrillators (ICD's) are also well known in the art. These devices generally include an arrhythmia detector that detects accelerated arrhythmias, such as tachycardia or fibrillation. When such a tachyarrhythmia is detected, a pulse generator delivers electrical therapy to the patient's heart. A therapy for tachycardia may be anti-tachycardia pacing and a therapy for fibrillation may be a defibrillating shock. Such therapies for both atrial and ventricular tachyarrhythmias are well known.

Implantable cardiac devices find usefulness beyond the provision of the aforementioned therapies. For example, such device may be very useful in the collection data for various types of studies relating to the heart or for monitoring the disease state of a patient.

One parameter commonly important in cardiac data collection is cardiac interval. Cardiac interval determination requires reliable R wave detection. Unfortunately, reliable R wave detection is difficult under many commonly found conditions. Such conditions include varying baseline and changing morphology such as varying R wave amplitude and reduced R/T ratio. The use of fixed threshold R wave detection, commonly found in implantable cardiac devices, makes it difficult to reliably detect the R waves under the noted conditions.

It is very important to be able to precisely detect R waves and accurately determine the starting time of that complex in case of co-morbidity detection. For example, it is known that hypoglycemia can be detected based on monitoring changes in the QT interval observed within an electrocardiogram (ECG), as well as based on observation of dispersion of QT intervals within the ECG. Studies in diabetics have also shown that hypoglycemia can be detected based on observation of a significant lengthening of the QTc interval occurring during spontaneous nocturnal hypoglycemia. R wave detection error is incorporated in the QT interval error as well. All of this leads to poor quality of data for co-morbidity detection and reduces the specificity of the diagnostic. This is true for all co-morbidity detections and any therapy that depends on precise detection of R waves.

SUMMARY

According to one embodiment, a method of precisely detecting the time of occurrence of a cardiac event of a heart comprises the steps of sensing electrical activity of the heart to generate an electrogram of the heart, applying the electrogram to an event detector having a plurality of spaced apart thresholds, the electrogram having an amplitude for crossing at least one of the thresholds, and determining a characteristic identifying feature of the electrogram at each threshold crossing of the electrogram. The method further comprises comparing the determined characteristic identifying features to an electrogram template, and identifying the time of occurrence of the cardiac event based upon the comparison.

The characteristic identifying may be one of electrogram slope, electrogram amplitude, and time of threshold crossing. The step of identifying the time of occurrence of the cardiac event based upon the comparison comprises the steps of assigning a point on the electrogram template as a fiducial point, aligning the electrogram with the electrogram template and locating a point on the electrogram corresponding to the fiducial point on the cardiac event template.

The cardiac event may be an R wave. The electrogram may be a portion of a cardiac cycle.

The method may further comprise the steps of defining a recording window and recording the electrogram during the recording window. The method may comprise the further step of initiating the recording window based upon real time detection of the cardiac event.

In another embodiment, a system that accurately detects the time of occurrence of a cardiac event of a heart comprises a sensing circuit that senses electrical activity of the heart to generate an electrogram of the heart, and an event detector that acts upon the electrogram. The event detector has a plurality of spaced apart thresholds. The thresholds are chosen such that the electrogram has an amplitude for crossing at least one of the thresholds. The system further comprises a processor that determines a characteristic identifying feature of the electrogram at each threshold crossing of the electrogram, compares the determined characteristic identifying features to an electrogram template, and identifies the time of occurrence of the cardiac event based upon the comparison.

The characteristic identifying feature may be electrogram slope. The characteristic identifying feature may be electrogram amplitude. The characteristic identifying feature may be time of threshold crossing.

The processer may be programmed to assign a point on the electrogram template as a fiducial point, align the electrogram with the electrogram template based upon the characteristic identifying features and locate a point on the electrogram corresponding to the fiducial point on the cardiac event template. The cardiac event may be an R wave.

The electrogram is preferably a portion of a cardiac cycle. The processor may further be programmed to define a recording window and to record the electrogram during the recording window. The processor may be further programmed to initiate the recording window based upon a real time detection of the cardiac event.

In a still further embodiment, an implantable cardiac device may include a system that accurately detects the time of occurrence of a cardiac event of a heart comprising a sensing circuit that senses electrical activity of the heart to generate an electrogram of the heart and an event detector that acts upon the electrogram. The event detector has a plurality of spaced apart thresholds and the thresholds are selected such that the electrogram has an amplitude for crossing at least one of the thresholds. The device further includes a processor that determines a characteristic identifying feature of the electrogram at each threshold crossing of the electrogram, compares the determined characteristic identifying features to an electrogram template, and identifies the time of occurrence of the cardiac event based upon the comparison.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
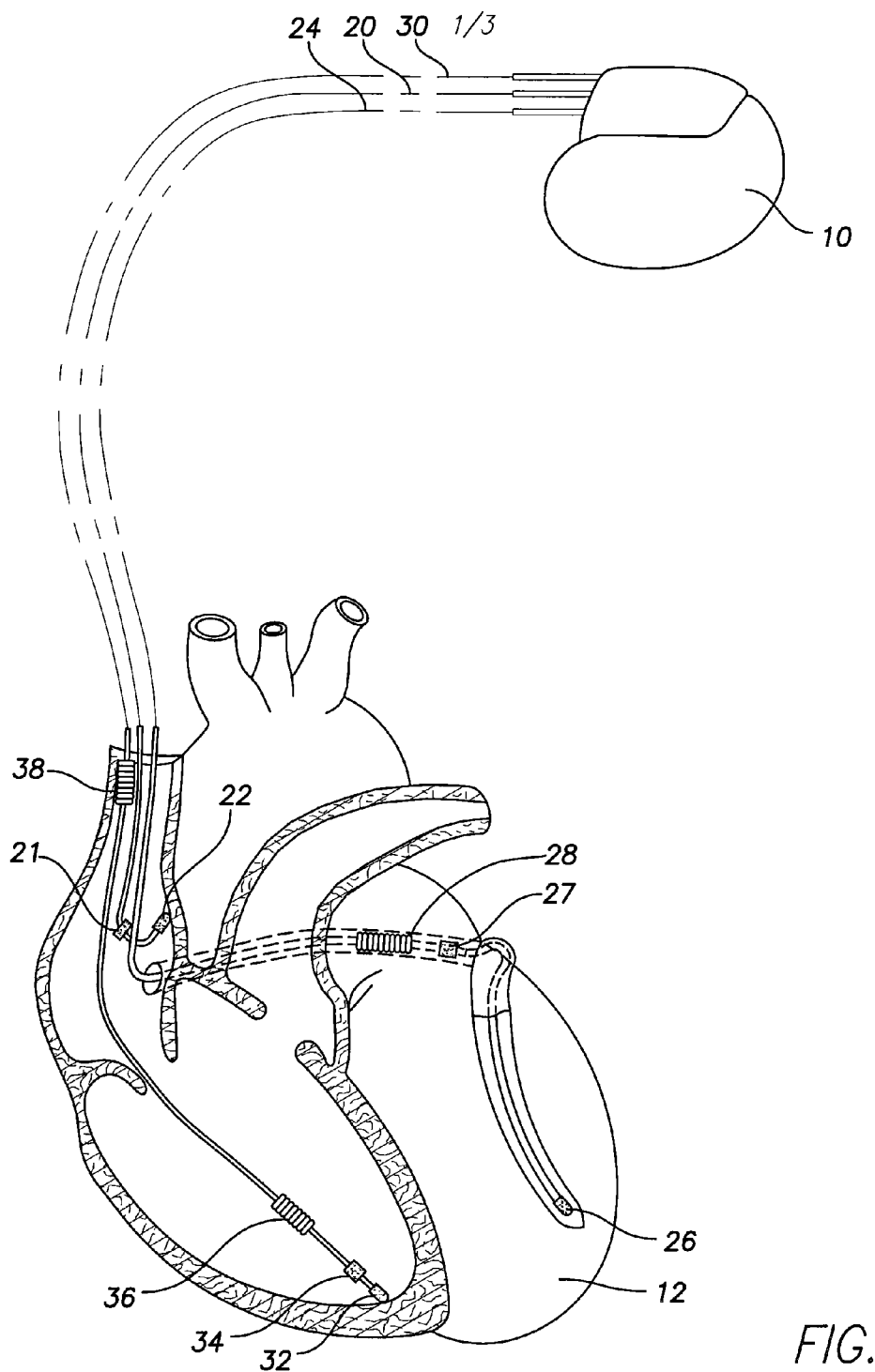
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
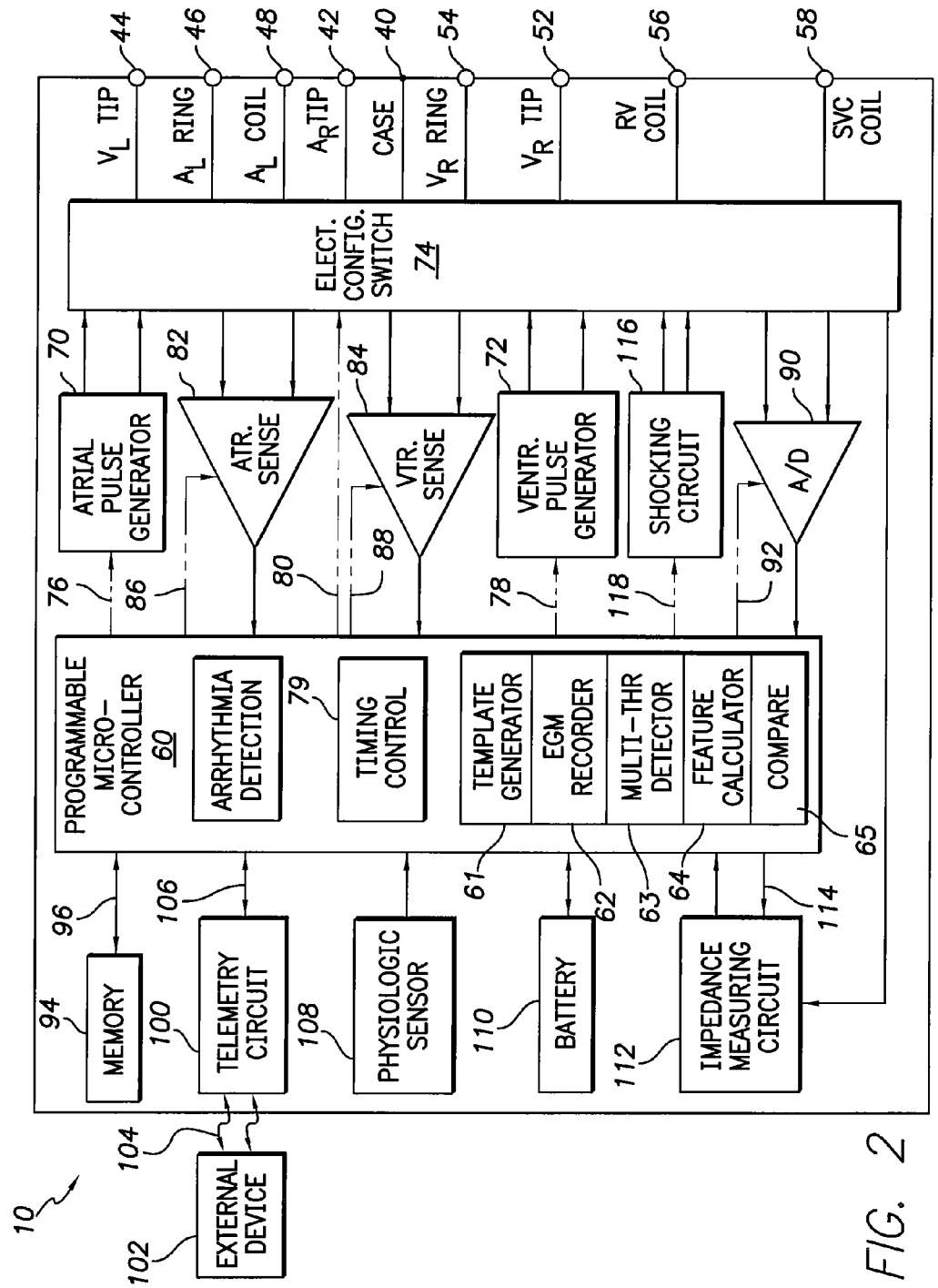
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. Either one of the pulse generators 70 and 72 may be employed for delivering stimulation pulses to or near to the AV node via electrode 22 or electrode 25.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. To that end, the timing control may control the time between individual pulses and the total time in which the pulse are delivered. The timing control 79 may further be used determine ventricular rate, for example.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, may receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

The device 10 further includes an arrhythmia detector 75 that utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. The physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With continued reference to FIG. 2, the device further includes a system for precisely detecting the time of occurrence of a cardiac event. While the embodiment described herein is directed towards precisely detecting the time of occurrence of R waves, the invention may be practiced to advantage for precisely timing the occurrence of other types of cardiac events as well including, for example, T waves and P waves, without departing from the present invention.

More particularly, as will be seen hereinafter according to this embodiment, the device establishes a template of the desire cardiac event. This may be accomplished by digitally recording a plurality of such events within a recording window, averaging the recorded events and then normalizing the result. Then, a plurality of thresholds is selected for waveform analysis. For example, four such thresholds may be defined, two positive and two negative. The upper and lower most thresholds are preferably selected so that a suitable guard band is present to provide a high probability that the intended signal levels will pass through at least one of the thresholds. A characteristic defining feature of the recorded signals is then selected for calculation for each threshold crossing. The characteristic defining feature may be one or any combination of signal slope, amplitude, or crossing time. Lastly, a point on the template (herein referred to as a fiducial point) is selected as the starting point of the selected cardiac event.

To accomplish the forgoing, the device includes a template generator 61, an electrogram (EGM) recorder 62, a multi-threshold detector 63, and a feature calculator 64. The template generator 61 may utilize the EGM recorder to set the recording windows and the data acquisition system 90 to perform the EGM recording. The multiple thresholds, once selected by the template generator 61, may be entered into the multi-threshold detector 63. The characteristic defining features, once selected, may be entered into the feature calculator 64.

The device 10 is now ready to record the selected cardiac EGM events. The recording may take place during the recording windows which may be timed off of event detection preformed by the event detector used for delivering therapy to the heart. Such a detector may be a single threshold event detector of the type well known in the art. Once the EGM's are normalized and stored, they may be applied retrospectively to the multi-threshold detector 63. Upon each threshold crossing, the characteristic defining feature is calculated by the feature calculator 64. Then, the characteristic identifying features are compared by the comparator 65 to the template at the threshold crossings. When the comparison indicates that the retrospectively recorded EGM is aligned with the template, the fiducial point on the template is used to locate the starting point of the cardiac event on the recorded EGM. The forgoing is then repeated for the remaining recorded cardiac events. If during the comparison the characteristic identifying features it is found that the characteristic identifying features of the recorded EGM is more that a certain amount different from that of the template, lack of a match is declared and the data for that recorded cardiac event is discarded.

Figure 3:
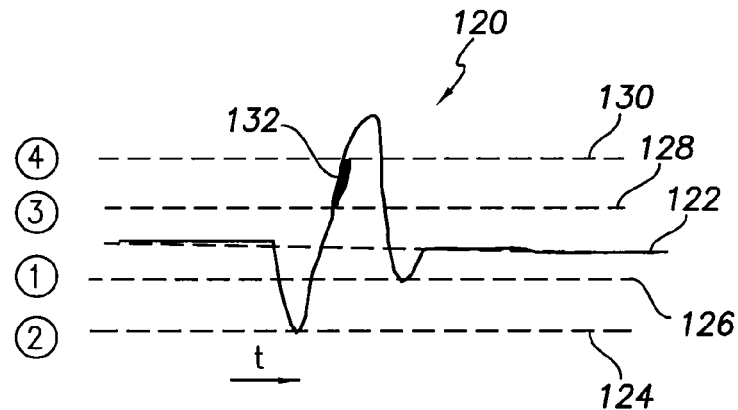
FIG. 3 is a representation of a template waveform imposed on a plurality of thresholds to lend a better understanding of the present invention.

The forgoing may be better understood by making reference to FIG. 3. where a template 120 according to an embodiment of the invention is illustrated. Here it may be seen that the template has been normalized about the zero axis 122. Four thresholds 124, 126, 128, and 130 gave been selected. As previously mentioned, the threshold are selected to have a sufficient guard band to assure the intended recorded cardiac events will exceed the thresholds.

In accordance with this embodiment, the characteristic identifying feature selected for the template is waveform slope. As previously mentioned, additional features may include amplitude or threshold crossing time. The fiducial point is taken to be located at the first signal crossing of threshold 128 at point 132. With the template 120 having been established, retrospective analysis of recorded cardiac events may now begin.

Figure 4:
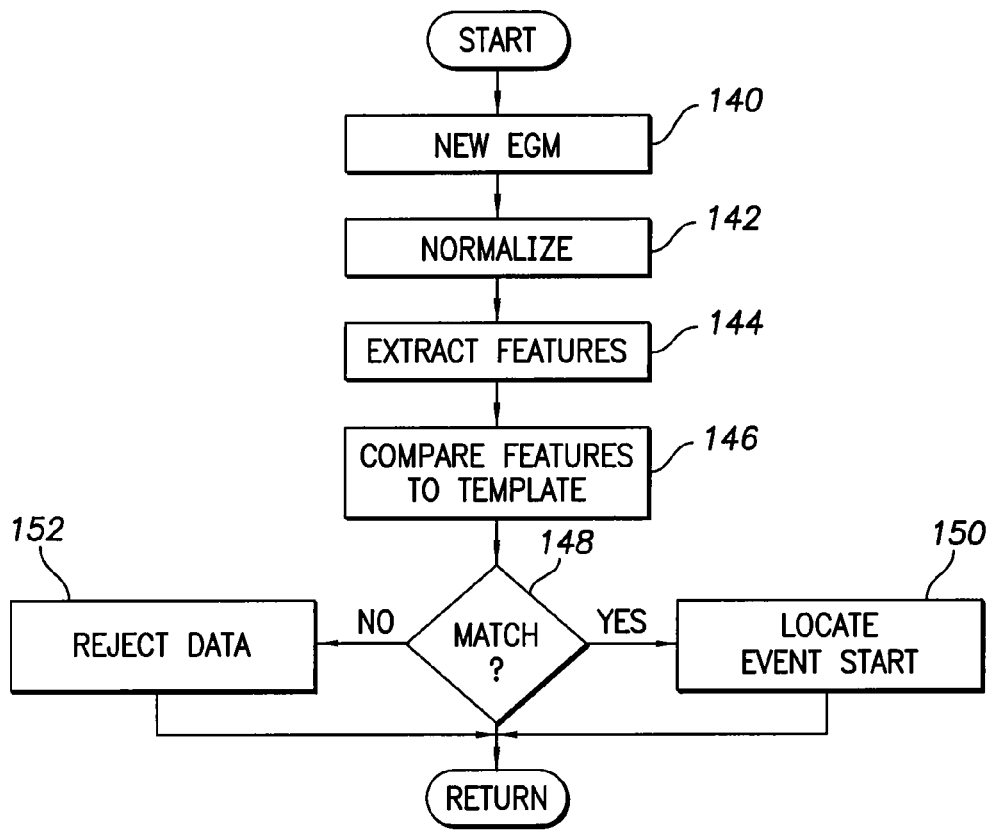
FIG. 4 is a flow chart describing an overview of the operation of an embodiment of the present invention.

In FIG. 4, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 4 initiates with activity block 140 wherein a new EGM recording of a cardiac event is fetched. Next, the recorded EGM is normalized in accordance with activity block 142. Next, in activity block 144, the EGM is applied to the multi-threshold detector 63, the slope thereof is calculated for each threshold crossing by the feature calculator 64 to extract the slope of the EGM at each threshold crossing. Next, in activity block 146, the comparator 65 compares the calculated slopes to the slopes of the template 120 at the respective threshold crossings. The similarity in the slopes is determined in decision block 148. If the slopes of the EGM are within a certain percentage of the slopes of the template 120 at the respective thresholds, the process advances to activity block wherein the starting point of the cardiac event is determined. As previously mentioned, this may be accomplished by locating the point on the EGM that corresponds to the fiducial point 132 in the template 120. Again, here, the fiducial point is the first crossing of the threshold 128 by the EGM. The process then returns for the analysis of the next recorded EGM.

If in decision block 148 it is found that the slopes of the EGM are not within a certain percentage of the slopes of the template 120 at the respective thresholds, the process moves to activity block 152. Here a data mismatch is declared and the EGM data is discarded. The process then returns.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of detecting the time of occurrence of a cardiac event of a heart, the method comprising:

sensing electrical activity of the heart to generate an electrogram of the heart;

applying the electrogram to an event detector having a plurality of thresholds, the electrogram having an amplitude for crossing a plurality of the thresholds;

determining a characteristic identifying feature of the electrogram at each of the plurality of threshold crossings of the electrogram;

comparing the determined characteristic identifying features to an electrogram template for each of the plurality of threshold crossings; and identifying the time of occurrence of the cardiac event based upon the comparison.

2. The method of claim 1, wherein the characteristic identifying feature is electrogram slope.

3. The method of claim 1, wherein the characteristic identifying feature is electrogram amplitude.

4. The method of claim 1, wherein the characteristic identifying feature is time of threshold crossing.

5. The method of claim 1, wherein the step of identifying the time of occurrence of the cardiac event based upon the comparison comprises the steps of assigning a point on the electrogram template as a fiducial point, aligning the electrogram with the electrogram template and locating a point on the electrogram corresponding to the fiducial point on the electrogram template.

6. The method of claim 1, wherein the electrogram is a portion of a cardiac cycle.

7. The method of claim 6, further comprising the steps of defining a recording window and recording the electrogram during the recording window.

8. The method of claim 7, comprising the further step of initiating the recording window based upon real time detection of the cardiac event.

9. A system that detects the time of occurrence of a cardiac event of a heart, the system comprising:

a sensing circuit that senses electrical activity of the heart to generate an electrogram of the heart;

an event detector that acts upon the electrogram, the event detector having a plurality of thresholds, the electrogram having an amplitude for crossing a plurality of the thresholds; and a processor that stores an electrogram template and determines a characteristic identifying feature of the electrogram at each of the plurality of threshold crossings of the electrogram, compares the determined characteristic identifying features to the electrogram template, and identifies the time of occurrence of the cardiac event based upon the comparison.

10. The system of claim 9, wherein the characteristic identifying feature is electrogram slope.

11. The system of claim 9, wherein the characteristic identifying feature is electrogram amplitude.

12. The system of claim 9, wherein the characteristic identifying feature is time of threshold crossing.

13. The system of claim 9, wherein the processer is programmed to assign a point on the electrogram template as a fiducial point, align the electrogram with the electrogram template based upon the characteristic identifying features and locate a point on the electrogram corresponding to the fiducial point on the electrogram template.

14. The system of claim 9, wherein the cardiac event is an R wave.

15. The system of claim 9, wherein the electrogram is a portion of a cardiac cycle.

16. The system of claim 15, wherein the processor is further programmed to define a recording window and to record the electrogram during the recording window.

17. The system of claim 16, wherein the processor is further programmed to initiate the recording window based upon a real time detection of the cardiac event.

18. In an implantable cardiac device, a system that detects the time of occurrence of a cardiac event of a heart comprising:
  a sensing circuit that senses electrical activity of the heart to generate an electrogram of the heart;
  an event detector that acts upon the electrogram, the event detector having a plurality of thresholds, the electrogram having an amplitude for crossing a plurality of the thresholds; and
  a processor that stores an electrogram template and determines a characteristic identifying feature of the electrogram at each of the plurality of threshold crossings of the electrogram, compares the determined characteristic identifying features to the electrogram template, and identifies the time of occurrence of the cardiac event based upon the comparison.

19. The device of claim 18, wherein the characteristic identifying feature is electrogram slope.

20. The device of claim 18, wherein the characteristic identifying feature is electrogram amplitude.

* * * * *